United States Patent [19]

Wanderer et al.

[11] Patent Number: 4,850,961
[45] Date of Patent: Jul. 25, 1989

[54] INDWELLING PLACEMENT DEVICE WITH GUARD

[76] Inventors: Alan A. Wanderer, 1075 E. Radcliffe, Englewood, Colo. 80110; William E. Sagstetter, 2217 E. Grove, Denver, Colo. 80210

[21] Appl. No.: 79,599

[22] Filed: Jul. 30, 1987

[51] Int. Cl.$^4$ .............................................. A61M 5/32
[52] U.S. Cl. ..................................... 604/53; 604/164; 604/198; 604/110; 604/263
[58] Field of Search ..................................... 604/51-53, 604/158-172, 192, 198, 263

[56] References Cited

U.S. PATENT DOCUMENTS

| | | | |
|---|---|---|---|
| 2,997,043 | 8/1961 | Flynn | 604/263 |
| 3,592,192 | 7/1971 | Narautuneian | 604/165 |
| 4,096,860 | 6/1978 | McLaughlin | 604/167 X |
| 4,160,450 | 7/1979 | Doherty | 604/162 X |
| 4,664,654 | 5/1987 | Strauss | 604/198 |
| 4,676,783 | 6/1987 | Jagger et al. | 604/171 |
| 4,725,267 | 2/1988 | Vaillancourt | 604/198 X |
| 4,762,516 | 8/1958 | Luther et al. | 604/164 |

*Primary Examiner*—Dalton L. Truluck
*Attorney, Agent, or Firm*—Cahill, Sutton & Thomas

[57] ABSTRACT

An indwelling placement device having an introducing needle and a catheter for infusing fluids into a blood vessel incorporates a guard for shielding the needle prior to extension from therewithin and for receiving the needle upon retraction thereinto to preclude an operator inadvertently contacting the needle after use. Once retracted, the needle cannot be extended from within the guard. Upon retraction of the needle into the guard, a button mates with the open end of a hollow hub of the needle to prevent outflow of residual blood therefrom. A valve is incorporated with the catheter to preclude blood outflow from the catheter upon withdrawal of the needle and prior to attachment of an intravenous line for conveying a fluid to be intravenously administered.

40 Claims, 3 Drawing Sheets

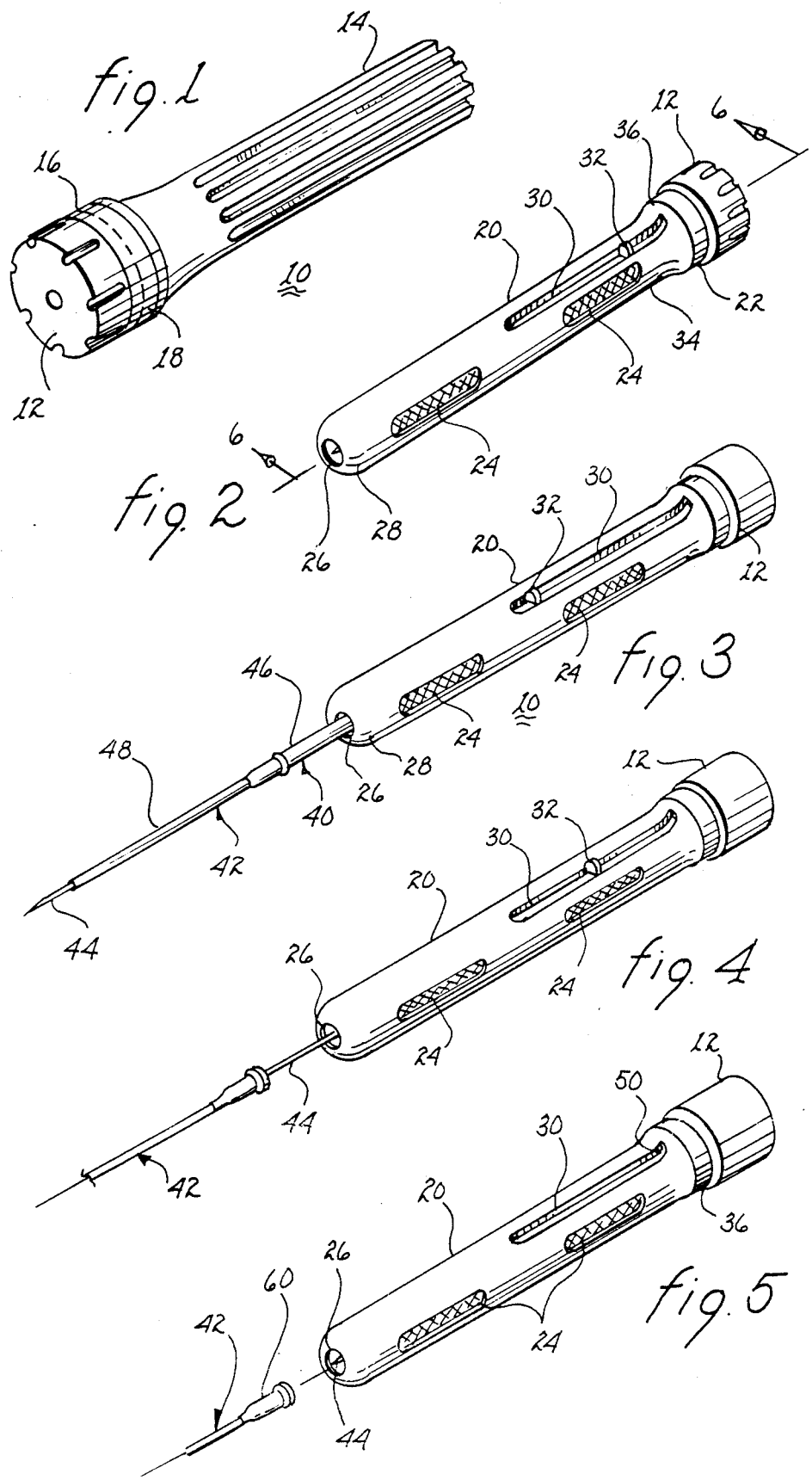

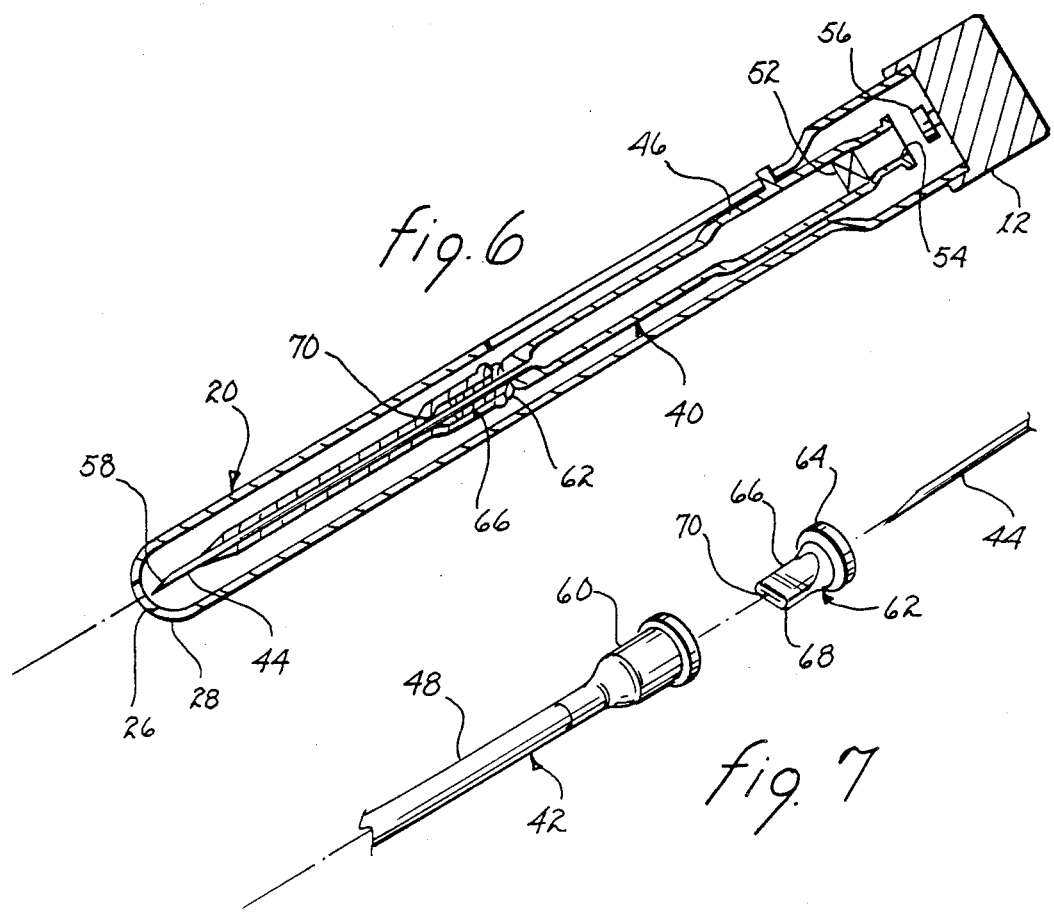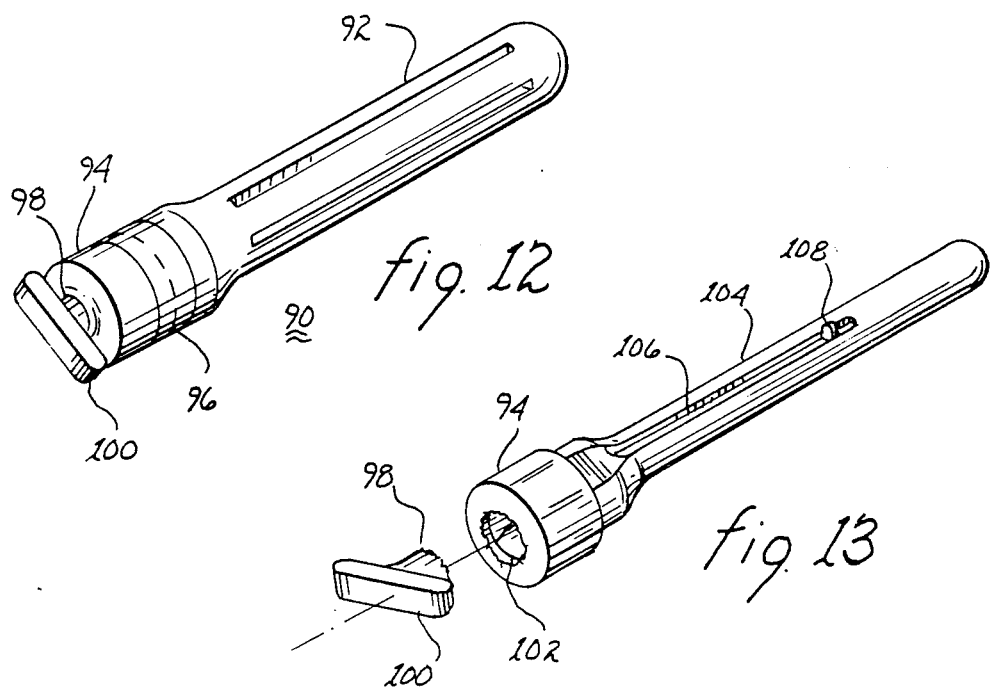

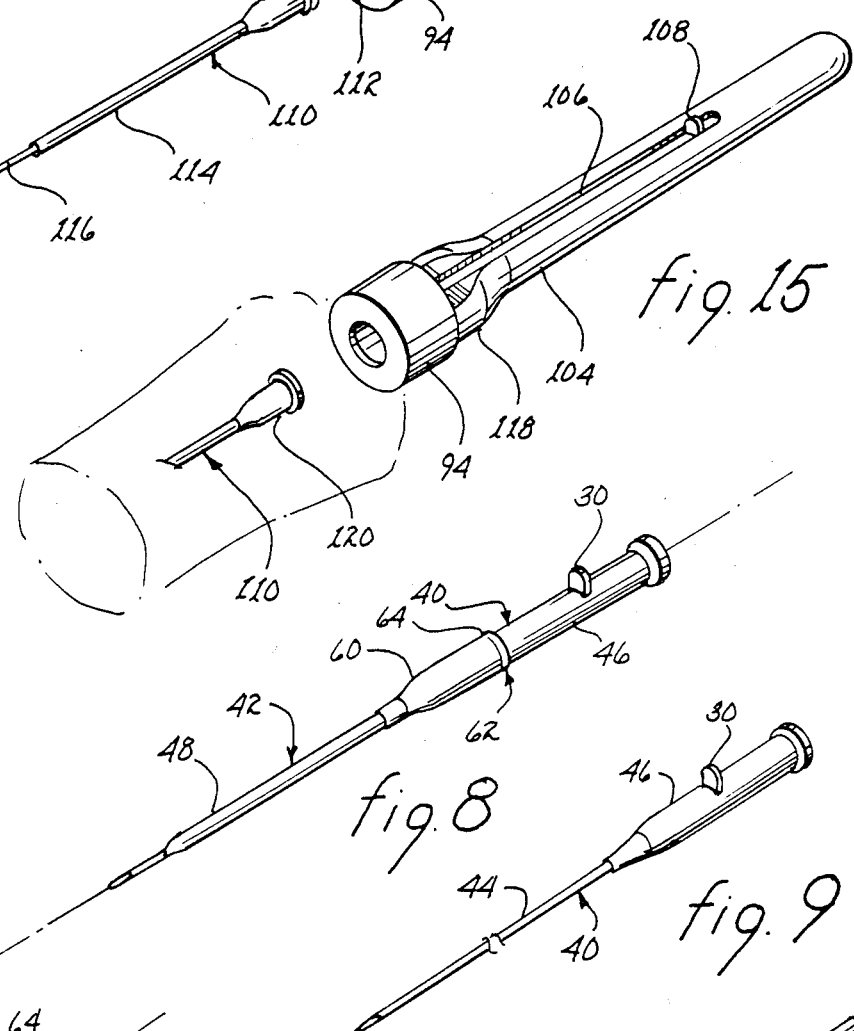

INDWELLING PLACEMENT DEVICE WITH GUARD

BACKGROUND OF THE INVENTION

1. Field of the Invention

The present invention relates to devices for protecting medical personnel from inadvertent contact with body fluids during a medical procedure and, more particularly, to a device for precluding needle stick and contamination by blood from a patient during intravenous insertion of a catheter.

2. Description of the Prior Art

The administration of medication or sustenance intravenously has been an accepted medical procedure for decades. The procedure contemplates the use of an introducer needle for introducing a needle circumscribing sheath into the vein of a patient. The sheath includes a hub for receiving a male member of an intravenous conduit connected to a source of the fluid to be injected. After insertion of the catheter, the needle is withdrawn. Such withdrawal creates an open passageway through the catheter and its hub through which blood from the vein will flow until the intravenous line is attached to the hub. It is not unusual for the administering medical personnel to be stuck with the needle during manipulation of the needle subsequent to withdrawal from the catheter. Even physical contact with the needle will expose the medical personnel to contact with any blood or other fluids in or upon the needle. Such contact with the blood and body fluids and needle stick exposes the attending medical personnel to a high risk of contracting serious infectious diseases, such as AIDS, infectious hepatitis, etc.

The problems attendant leakage of blood during the procedure of inserting a catheter are well known and various attempts have been made to at least reduce, if not eliminate, such leakage and exposure to contact. U.S. Pat. No. 4,512,766 is directed to a puncturable self sealing valve at the hub of the catheter to close the exposed end of the catheter upon withdrawal of the needle. During attachment of the intravenous conduit, the valve is forced upon to establish communication with the catheter. Depending upon the degree of resiliency of the valve, one or more droplets of blood may or may not flow therethrough during the step of withdrawing the penetrably mounted needle. No apparatus is suggested or described for protecting medical personel against contact with the needle or needle stick, either before or after use. U.S. Pat. Nos. 4,192,304 and 4,198,973 are directed to a pair of tabs manually foldable upon one another to pinch the catheter tube after insertion and prior to attachment of an intravenous line. Depending upon the manual dexterity of the operator and the quickness with which the catheter line is pinched shut during withdrawal of the needle, a lesser or greater amount of blood will be expelled from the catheter. It may be noted that the catheter must be continually pinched until attachment of the intravenous line to prevent outflow of blood.

U.S. Pat. No. 4,629,450 is directed to apparatus for introducing a catheter into a blood vessel and includes a dilator member. A valve is incorporated to prevent blood outflow from the apparatus during insertion of the catheter. Exposure of medical personnel to the blood contaminated surface of the withdrawn needle and dilator and to needle stick is not addressed.

U.S. Pat. No. 3,709,223 is directed to an intravenous catheter placement unit which includes a sheath. The purpose of the sheath is to prevent escape of blood from the open end of the needle hub. U.S. Pat. No. 3,595,230 is directed to a flexible tubular shield for enclosing a catheter and a needle. A slot disposed in the shield permits extension of a tab therethrough for penetrable extension of the needle through a frictionally engaged end plug of the shield. Necessarily, longitudinal collapse of the shield is necessary to effect extension of the needle. Retraction of the needle into the sheath appears not to be intended.

U.S. Pat. No. 3,572,334 is directed to a catheter circumscribed by a needle and the invention is directed to a protective sheath for minimizing the likelihood of needle penetration of the catheter. To avoid the likelihood of catheter penetration, the present state of the art devices locates the catheter as a sheath about the needle.

U.S. Pat. No. 4,445,893 is directed to a stabilizing member for stabilizing the catheter upon a patient. It also illustrates and describes the state of the art in intravenous catheter infusion devices which are presently used by the medical profession. The exposed needle can become contaminated before use since the shield is removed from the needle assembly and catheter. Furthermore, it is possible to reinsert the needle into the catheter to reposition a non functioning blood flowing catheter; such reinsertion may cause severance of parts of the catheter, causing potential embolization of the catheter parts into the blood circulation. Blood can leak from the catheter prior to it being plugged or attached to an intravenous line.

SUMMARY OF THE PRESENT INVENTION

The present invention is directed to an indwelling placement device for inserting an intravenous catheter without incurring a flow of blood from the catheter during the time between removal of the needle and attachment of an intravenous line. A non flexible guard is incorporated to shield the needle against accidental contact or needle stick prior to vein puncture and concomitantly with withdrawal of the needle. Upon retraction of the needle into the guard, the open ended hub of the needle is sealed to discourage blood outflow from within the passageway of the needle. Sealing means are incorporated to maintain the indwelling placement device sterile prior to use and the configuration of the guard permits disposal without exposing the attending medical personnel to a likelihood of needle stick or contact with any body fluids in or about the needle.

It is therefore a primary object of the present invention to reduce the exposure of medical personnel to infectious diseases during a vein puncture procedure.

Another object of the present invention is to provide an introducer needle mounted catheter which precludes an outflow of blood after removal of the needle and prior to attachment of an intravenous line.

Still another object of the present invention is to provide an indwelling placement device with a guard for shielding medical personnel from contact with the needle before, during and after implantation of a catheter.

Yet another object of the present invention is to provide a non-disengagable guard for use with a needle assembly of an indwelling placement device.

A further object of the present invention is to provide a guard assembly for retractingly retaining and preventing blood flow from within a needle of an indwelling placement device.

A still further object of the present invention is to provide a sterile indwelling placement device.

A still further object of the present invention is to permit recovery of a needle of an emplacement device with one hand and to permit hook up of the intravenous line into the catheter with the other hand.

A still further object of the present invention is to provide a guard assembly wherein the guard can be manipulated to improve accurate guiding of the extended needle and catheter into the blood vessel.

A still further object of the present invention is to provide a guard assembly for enclosing and locking the introducer needle of an indwelling plant device after use to shield the needle and prevent reuse of the needle.

A still further object of the present invention is to provide an indwelling placement device for exteriorizing the needle assembly from within a guard without manually handling the introducer needle and the catheter.

A still further object of the present invention is to provide a self contained sterile indwelling placement device which can be sterilized by state of the art gamma radiation.

A yet further object of the present invention is to provide a method for preventing a flow of blood from a catheter during and subsequent to installation and prior to attachment of an intravenous line.

A yet further object of the present invention is to provide a method for shielding the needle assembly of an indwelling placement device to protect medical personnel against accidental needle stick and contact with the needle.

These and other objects of the present invention will become apparent to those skilled in the art as the description proceeds.

BRIEF DESCRIPTION OF THE DRAWINGS

FIG. 1 is a perspective view illustrating the sealed and sterile configuration of the present invention;

FIG. 2 is a perspective view illustrating the present invention prior to extension of the needle assembly with removal of a disposable shield;

FIG. 3 illustrates extension of the needle assembly from the guard;

FIG. 4 illustrates insertion of the catheter;

FIG. 5 illustrates withdrawal of the needle from the catheter and retraction of the needle into the guard;

FIG. 6 is a cross sectional view taken along lines 6—6, as shown in FIG. 2;

FIG. 7 illustrates a valve usable in conjunction with the catheter;

FIG. 8 illustrates the catheter and joined needle assembly;

FIG. 9 illustrates the needle assembly;

FIG. 10 illustrates the catheter assembly;

FIGS. 11a and 11b illustrate a valve usable in combination with the catheter assembly;

FIG. 12 illustrates the sealed and sterile configuration of a variant of the present invention;

FIG. 13 illustrates a frangible tab of the variant for accommodating extension of the needle assembly with removal of a disposable shield;

FIG. 14 illustrates extension of the needle assembly from the guard of the variant; and FIG. 15 illustrates retraction of the needle assembly into the guard of the variant.

DESCRIPTION OF THE PREFERRED EMBODIMENT

Referring to FIG. 1, there is illustrated an indwelling placement device 10 having an external structure for maintaining the operative elements sterile prior to use. The structure includes an end cap 12 for supportingly engaging a disposable generally cylindrically shaped closed end shield 14. Junction 16 (shown in dashed lines) between the cap and the shield is sealed with a length of sterile tape 18 extending thereabout. It may be noted that the cap and the shield provide protection against both damage and contamination to the internally located element and are intended to withstand normally expected handling and abusive manipulation.

Upon removal of tape 18 and disengagement of shield 14 from end cap 12, whether by sliding or unscrewing, a guard 20, as shown in FIG. 2, is exposed. The guard is permanently and rigidly attached to cap 12. It may also include an annular supporting surface 22 for engagement with a corresponding interior surface of shield 14. Alternatively, surface 22 may be threaded for threaded engagement with the shield.

Guard 20 is preferably of relatively rigid material to prevent bending, distension and compression, both longitudinally and axially, of the guard. The guard may include a plurality of cross hatched or other high friction areas 24 to assist in non sliding manual gripping of the guard. An aperture 26 is disposed at anterior end 28 of the guard to accommodate extension and retraction therethrough of a needle assembly. A longitudinally aligned slot 30 is formed in guard 20 to guide and accommodate translatory movement of tab 32. The tab is functionally, if not mechanically, associated with the needle assembly to assist in extension and retraction of the needle assembly. Posterior end 34 of guard 20 includes an annularly expanded section 36. Slot 30 extends into section 36 to accommodate translatory movement of tab 32 into section 36 where it becomes unreachable and irretrievable. Depending upon manufacturing and other mechanical considerations, cap 12 may be formed as a part of or separate from guard 20 and later assembled therewith.

In preparation for use of indwelling placement device 10, shield 14 is removed, as described above. By grasping guard 20 between one's fingers and against area 24, tab 30 may be translated anteriorly with one's thumb. Such translation of the tab produces a commensurate rectilinear translation of needle assembly 40 and catheter assembly 42 mounted thereon (see FIG. 8, 9 and 10). It may be noted that extension of the needle assembly can be done single handedly by medical personnel. It is to be further noted that the extension is performed from a point posteriorly of anterior end 28 which assists in maintaining the hand and other body parts of the medical personnel posteriorly of the needle assembly.

Upon introduction of needle 44 into the vein of a patient, a flow of blood will occur through the needle into hub 46. Preferably, the hub is transparent, or at least translucent, to permit medical personnel to visualize the presence of blood therein to confirm correct positioning of the needle within the vein. Thereafter, catheter assembly 42 is slid anteriorly along needle 44 to locate sleeve 48 of the catheter within the vein. Upon posterior translational movement of tab 32 along slot 30, needle 44 will be withdrawn from within catheter assembly 42 as illustrated in FIG. 4.

Upon completion of translation of tab 32, the tab will become located within posterior end 50 of slot 32 and generally coincident with annular expanded section 36. In this position, the tab is essentially inaccessible. Concomitantly, needle 44 will have been withdrawn or retracted into guard 20, as illustrated in FIG. 5. It may be pointed out that during retraction of the needle assembly, all manipulation by medical personnel is performed posteriorly of anterior end 28 and there exists no need for the medical personnel to be directly or indirectly in contact with the surface or point of the needle. Such lack of contact will minimize the potential for exposure to any body fluids of the patient upon the surface of the needle and the possibility of needle stick will also be minimized. After retraction of the needle, as illustrated in FIG. 5, guard 20 may be handled without fear of needle stick or contact with the surface of the needle as the needle is completely enclosed within the guard.

As is conventional, hub 46 of needle assembly 40 includes a filter 52 at the posterior end, as illustrated in FIG. 6. This filter permits escape of air from within the needle assembly in response to an inflow of blood through needle 44. Additionally, the filter will have a tendency to prevent an outflow of blood from the hub. Upon complete retraction of needle assembly 40, as illustrated in FIG. 5, open end 54 of hub 46 will circumscribingly engage a plug or button 56 in a snap fit manner to retain needle assembly 40 secured to cap 12. Such retention will tend to prevent inadvertent anterior movement of retracted needle assembly 40 due to forces imposed upon the indwelling placement device. The snap fit engagement, if also reasonably air tight, will tend to discourage outflow of blood from opening 58 of needle 44 due to creation of an air lock within hub 46. Accordingly, dripping of blood from needle 44 to the interior surface of guard 20 is constrained. The radially inward orientation of guard 20 at anterior end 28 defining aperture 26 will serve in the manner of a dam to discourage outflow of blood through aperture 26.

Upon installation of catheter assembly 42, as illustrated in FIG. 5, an outflow of blood from the vein may occur through hub 60 if such outflow is not restrained by blocking the opening of the hub or other means. Blocking the opening of the hub, which is present standard practice, is essentially incapable of precluding at least outflow of a droplet or two of blood. Since contact by medical personnel of even a drop of blood may expose them to fatal infectious diseases that may be carried by the patient, such exposure should be eliminated. Referring to FIGS. 7, 8, 10, 11a and 11b there is illustrated a valve 62 for eliminating any outflow of blood from hub 60 prior insertion of the male end of an intravenous line. Valve 60 includes an annular band 64 fixated with hub 60 to retain the valve in place with the hub. A skirt 66 extends from band 64. Terminal end 68 of the skirt includes a normally closed slit 70.

The operation of valve 62 may be described as follows. Any pressure exerted by fluid within hub 60 will bear against the external surface of skirt 66 to encourage closure of slit 70. With such closure of the slit, fluid flow through the valve will be precluded. If, upon insertion of the male end of a intravenous line into hub 60 containing valve 62, the pressure exerted by the fluid within the intravenous line attached to the hub is greater than the pressure of the blood within the hub acting upon the exterior of the skirt 66, the skirt will be expanded and slit 70 will be opened, as illustrated in FIG. 11b. Such opening will permit a flow of fluid into catheter assembly 42 and the vein of the patient. By inspection, it will be evident that a fluid can also be introduced into the vein through catheter assembly 42 by insertion of the male end of the intravenous line through valve 62. Such insertion would cause skirt 66 to open sufficiently to pass the male end of the intravenous line while exerting a gripping force to aid in retaining the male end in penetrable engagement with valve 62 and hub 60. Withdrawal of the male end would be related to the withdrawal of needle 44 described below and valve 62 would provide the same benefits of automatic closure to prevent an outflow of blood.

It may be noted, that the function and operation of valve 62 is not disturbed by mounting the catheter assembly upon the needle assembly, as illustrated in FIG. 6. Needle 44 simply extends through skirt 66 and slit 70. On withdrawal of needle 44, as illustrated in FIG. 4, slit 70 will close commensurate with passage of the end of the needle therethrough and prevent an outflow of blood.

Referring jointly to FIGS. 12 through 15, there is illustrated a variant 90. The variant includes a shield 92 removably attached to a cap 94 at junction 96, illustrated in dashed lines. A length of tape 98 disposed about the junction maintains the interior of variant 90 sterile. Cap 94 includes a frangible tab 98, which may include a handle 100 for assisting in removal of the tab.

Upon removal of tape 98 and shield 92, a guard 104 for shielding an intravenous catheter is exposed. Upon removal of the tab, as illustrated in FIG. 13, an aperture 102 is formed in cap 94. The guard includes a slot 106 to accommodate rectilinear translatory movement of tab 108. Movement of the tab anteriorly toward cap 94, as illustrated in FIG. 14, extends catheter assembly 110 and needle assembly 112 through aperture 102 in cap 94. Variant 90 is now ready for use to insert sleeve 114 of catheter assembly 110 into the vein of a patient, as illustrated in FIG. 15. It may be noted that translation of tab 108 may be effected by gripping guard 104 with a user's fingers and pushing upon the tab with the user's thumb. Furthermore, it may be noted that manipulation of the variant is posteriorly of cap 94.

After emplacement of catheter assembly 110, as illustrated in FIG. 15, needle assembly 112 is retracted into guard 104. Such retraction is effected by translation of tab 108 posteriorly from cap 94. On positioning tab 108 at the terminal end of slot 106, needle 116 will be fully retained within cap 94 and/or needle guard 104. The expanded annular section 118 of the guard may be of assistance to medical personnel in using only one hand to translatably reposition tab 108. Beads extending toward one another from opposed sides of the slot may be employed to frictionally retain the tab in one or another predetermined position.

From the above description it will be evident that guard 104 will maintain sterile the catheter and needle assemblies prior to use. Secondly, installation of the catheter does not require any touching or manipulation of the catheter assembly or needle assembly by medical personnel. Thirdly, on retraction of the needle assembly, it is fully enclosed within guard 104 to prevent the possibility of needle stick and such enclosure will minimize or preclude exposure to medical personnel from any of the patient's body fluids which potentially might transmit infectious diseases. Fourthly, variant 90, as depicted in FIG. 15, may be discarded after use without further precautions.

Catheter assembly 110 of variant 90 may incorporate in hub 120 a valve mechanism, such as valve 62 previously described. With such valve, the benefits attendant catheter assembly 42 will also be present for catheter assembly 110.

It is to be understood that various detents might be incorporated to positionally restrain the tab in one or another predetermined position along the respective slot. Furthermore, the exterior configuration of either of guards 20 or 104 may be modified to assist in single handed or multi handed manipulation.

While the principles of the invention have now been made clear in an illustrative embodiment, there will be immediately obvious to those skilled in the art many modifications of structure, arrangement, proportions, elements, materials, and components, used in the practice of the invention which are particularly adapted for specific environments and operating requirements without departing from those principles.

We claim:

1. An indwelling placement device for protecting personnel against accidental needle stick and contact with body fluids of a patient, said device comprising in combination:
   (a) a needle assembly said needle assembly including a hub for supporting said needle assembly;
   (b) a catheter assembly demountably mounted on said needle assembly for indwelling placement;
   (c) guard means initially enclosing and shielding said needle assembly and said mounted catheter assembly;
   (d) means for extending said needle assembly and said catheter assembly from said guard means and by rectilinearly translating said hub within said guard means;
   (e) means for retracting said needle assembly from said catheter assembly for indwelling placement of said catheter assembly and to enclose said needle assembly within said guard means; and
   (f) said guard means being formed of a single element having a passageway disposed therein for supporting and guiding said hub of said needle assembly to accommodate rectilinear translation of said needle assembly during extension and retraction of said needle assembly.

2. The device as set forth in claim 1 wherein said retracting means includes means for discouraging extension of said needle assembly after retraction.

3. The device as set forth in claim 1 wherein said retracting means includes a tab for manipulating extension and retraction of said needle assembly.

4. The device as set forth in claim 3 wherein said guard includes a slot for penetrably receiving said tab and for guiding said tab during extension and retraction of said needle assembly.

5. The device as set forth in claim 4 including means for shielding access to said tab after retraction of said needle assembly.

6. The device as set forth in claim 5 wherein said guard includes an expanded annular section and wherein said shielding means includes an extension of said slot extending into said expanded annular section.

7. The device as set forth in claim 4 including valve means for limiting fluid outflow from said catheter assembly.

8. The device as set forth in claim 7 wherein said catheter assembly includes a sleeve and a hub extending from said sleeve and wherein said valve means is disposed within said hub.

9. The device as set forth in claim 8 wherein said valve means includes means for accommodating penetrable engagement of said needle assembly.

10. The device as set forth in claim 7 including a cap disposed at the posterior end of said guard for closing the posterior end of said guard and means for accommodating penetration of said needle assembly at the anterior end of said guard.

11. The device as set forth in claim 10 wherein said needle assembly includes a hub disposed the posterior end of said needle assembly and wherein said cap includes a button for engaging and retaining said needle assembly hub upon retraction of said needle assembly.

12. The device as set forth in claim 10 including a shield for receiving and for enclosing said guard and means for securing said shield with said cap to protect said guard.

13. The device as set forth in claim 7 including a cap disposed at the anterior end of said guard, said cap including means for exteriorizing said needle assembly and said catheter assembly.

14. The device as set forth in claim 13 including a shield for receiving and enclosing said guard and means for securing said shield with said cap to protect said guard and maintain said needle assembly and said catheter assembly within said guard sterile.

15. The device as set forth in claim 13 wherein said guard includes means for developing an opening at the anterior end of said guard to permit exteriorizing at least a part of said needle assembly therethrough.

16. The device as set forth in claim 15 wherein said developing means comprises a twist off tab.

17. The device as set forth in claim 1 including valve means for limiting fluid outflow from said catheter assembly.

18. The device as set forth in claim 1 including means for precluding disengagement between said needle assembly and said guard.

19. The device as set forth in claim 1 including means for precluding translation of said guard past the point of said needle assembly to accommodate all manipulation of said guard from a location posteriorly of the point of said needle assembly.

20. The device as set forth in claim 1 wherein said guard includes means for developing an opening at the anterior end of said guard to permit exteriorizing at least a part of said needle assembly therethrough.

21. The device as set forth in claim 20 wherein said developing means comprises a twist off tab.

22. An indwelling placement device for protecting medical personnel against accidental needle stick and contact with body fluids of a patient, said device comprising in combination:
   (a) a needle assembly;
   (b) a catheter assembly demountably mounted on said needle assembly for indwelling placement;
   (c) guard means initially enclosing and shielding said needle assembly and said mounted catheter assembly;
   (d) means for extending said needle assembly and said catheter assembly from said guard means;
   (e) means for retracting said needle assembly from said catheter assembly for indwelling placement of said catheter assembly and to enclose said needle assembly within said guard means, said retracting means including a tab for manipulating extension and retraction of said needle assembly; and (f) means for shielding access to said tab after retraction of said needle assembly.

23. The device as set forth in claim 22 wherein said guard means includes a slot for penetrably receiving said tab and for guiding said tab during extension and retraction of said needle assembly.

24. An indwelling placement device for protecting medical personnel against accidental needle stick and contact with body fluids of a patient, said device comprising in combination:

(a) a needle assembly;

(b) a catheter assembly demountably mounted on said needle assembly for indwelling placement, said catheter assembly including a sleeve and a hub extending from said sleeve, said hub including valve means disposed within said hub for limiting fluid outflow from said catheter assembly;

(c) guard means initially enclosing and shielding said needle assembly and said mounted catheter assembly;

(d) means for extending said needle assembly and said catheter assembly from said guard means; and (e) means for retracting said needle assembly from said catheter assembly for indwelling placement of said catheter assembly and to enclose said needle assembly within said guard means.

25. The device as set forth in claim 24 wherein said valve means includes means for accommodating penetrable engagement of said needle assembly.

26. The device as set forth in claim 24 wherein said valve means includes a skirt having first and second ends, said skirt defining an opening at the first end and a normally closed slit at the second end.

27. An indwelling placement device for protecting medical personnel against accidental needle stick and contact with body fluids of a patient, said device comprising in combination:

(a) a needle assembly;

(b) a catheter assembly demountably mounted on said needle assembly for indwelling placement;

(c) guard means initially enclosing and shielding said needle assembly and said mounted catheter assembly;

(d) means for accommodating penetration of said needle assembly and said catheter assembly at the anterior end of said guard means;

(e) means for retracting said needle assembly from said catheter assembly for indwelling placement of said catheter assembly and to enclose said needle assembly within said guard means; and (f) a cap disposed at the posterior end of said guard means for closing the posterior end of said guard means.

28. The device as set forth in claim 27 wherein said needle assembly includes a hub disposed in the posterior end of said needle assembly and wherein said cap includes a button for engaging and retaining said needle assembly hub upon retraction of said needle assembly to establish an air lock within said needle assembly and prevent outflow of blood from said needle assembly.

29. An indwelling placement device for protecting medical personnel against accidental needle stick and contact with body fluids of a patient, said device comprising in combination:

(a) a needle assembly;

(b) a catheter assembly demountably mounted on said needle assembly for indwelling placement;

(c) guard means initially enclosing and shielding said needle assembly and said mounted catheter assembly;

(d) means for extending said needle assembly and said catheter assembly from said guard means;

(e) means for retracting said needle assembly from said catheter assembly for indwelling placement of said catheter assembly and to enclose said needle assembly within said guard means;

(f) a cap disposed at the posterior end of said guard means;

(g) a shield for receiving and for enclosing said guard means; and (h) means for securing said shield with said cap to protect said guard means.

30. The device as set forth in claim 29 including means for sealing said shield with said cap to maintain said needle assembly and said catheter assembly within said guard sterile.

31. A method for protecting medical personnel against needle stick and contact with body fluids of a patient during installation of an intravenous catheter, said method comprising the steps of:

(a) extending a needle assembly supporting a catheter assembly from within a passageway formed in a single element needle enclosing guard;

(b) penetrating the vein of a patient with the needle assembly and the catheter assembly;

(c) disengaging the needle assembly from the catheter assembly to leave the catheter assembly extending from the patient and in fluid communication with the vein of a patient;

(d) retracting the needle assembly into the passageway within the singular element guard to enclose the needle assembly therein; and (e) discouraging extension of the needle assembly from within the passageway after carrying out said retraction step.

32. The method as set forth in claim 30 wherein said step of withdrawing and said step of retracting are carried out simultaneously.

33. The method as set forth in claim 31 wherein said discouraging step includes the step of locking the needle assembly within the guard.

34. The method as set forth in claim 31 wherein said discouraging step includes the step of rendering inaccessible the needle assembly upon exercise of said retracting step.

35. A method for protecting medical personnel against needle stick and contact with body fluids of a patient during installation of an intravenous catheter, said method comprising the steps of:

(a) extending a needle assembly supporting a catheter assembly from within a needle enclosing guard;

(b) penetrating the vein of a patient with the needle assembly and the catheter assembly;

(c) disengaging the needle assembly from the catheter assembly to leave the catheter assembly extending from the patient and in fluid communication with the vein of a patient and separated from the needle assembly;

(d) inhibiting outflow of body fluids through a catheter assembly upon exercise of said disengaging step;

(e) retracting the needle assembly into the guard to enclose the needle assembly therein; and (f) discouraging extension of the needle assembly after carrying out said retracting step.

36. The method as set forth in claim 35 wherein a valve is associated with the catheter assembly and said inhibiting step comprises the step of limiting fluid flow in one direction through the valve.

37. A method for protecting medical personnel against needle stick and contact with body fluids of a patient during installation of an intravenous catheter, said method comprising the steps of:
  (a) extending a needle assembly supporting a catheter assembly from within a needle enclosing guard;
  (b) shielding the guard and the needle and catheter assemblies enclosing therein against contamination prior to exercise of said extending step;
  (c) penetrating the vein of a patient with the needle assembly and the catheter assembly;
  (d) disengaging the needle assembly from the catheter assembly to leave the catheter assembly extending from the patient and in fluid communication with the vein of the patient and separated from the needle assembly;
  (e) retracting the needle assembly into the guard to enclose the needle assembly therein; and
  (f) discouraging extension of the needle assembly after carrying out said retracting step.

38. A method for protecting medical personnel against needle stick and contact with body fluids of a patient during installation of an intravenous catheter, said method comprising the steps of;
  (a) extending a needle assembly supporting a catheter assembly from within a needle enclosing guard;
  (b) penetrating the vein of a patient with the needle assembly and the catheter assembly;
  (c) disengaging the needle assembly from the catheter assembly to leave the catheter assembly extending from the patient and in fluid communication with the vein of the patient and separated from the needle assembly;
  (d) inhibiting outflow of body fluids through the catheter assembly upon exercise of said withdrawing step;
  (e) retracting the needle assembly into the guard to enclose the needle assembly therein, said step of retracting being carried out simultaneously with said step of withdrawing; and
  (f) discouraging extension of the needle assembly after carrying out said retracting step.

39. The method as set forth in claim 38 wherein a valve is associated with the catheter assembly and said inhibiting step comprises the step of limiting fluid flow in one direction through the valve.

40. The method as set forth in claim 59 including the step of introducing a fluid through the valve of the catheter assembly and into the vein of a patient.

* * * * *